(12) United States Patent
Miraki

(10) Patent No.: US 10,555,732 B2
(45) Date of Patent: Feb. 11, 2020

(54) DEVICES AND METHODS FOR SUTURING A CARDIAC IMPLANT

(71) Applicant: EDWARDS LIFESCIENCES CORPORATION, Irvine, CA (US)

(72) Inventor: Manouchehr A. Miraki, Laguna Hills, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 415 days.

(21) Appl. No.: 15/326,567

(22) PCT Filed: Jul. 16, 2015

(86) PCT No.: PCT/US2015/040782
§ 371 (c)(1),
(2) Date: Jan. 16, 2017

(87) PCT Pub. No.: WO2016/011275
PCT Pub. Date: Jan. 21, 2016

(65) Prior Publication Data
US 2018/0206838 A1 Jul. 26, 2018

Related U.S. Application Data

(60) Provisional application No. 62/025,117, filed on Jul. 16, 2014.

(51) Int. Cl.
*A61B 17/06* (2006.01)
*A61F 2/24* (2006.01)
*A61B 17/04* (2006.01)

(52) U.S. Cl.
CPC .. *A61B 17/06004* (2013.01); *A61B 17/06123* (2013.01); *A61B 2017/0406* (2013.01);
(Continued)

(58) Field of Classification Search
CPC .............. A61B 17/06; A61B 17/06004; A61B 17/06123; A61B 2017/0406; A61B 2017/06028; A61B 17/06066
See application file for complete search history.

(56) References Cited

U.S. PATENT DOCUMENTS 6,626,930 B1  9/2003  Allen et al.
7,049,244 B2  5/2006  Becker et al.
(Continued)

FOREIGN PATENT DOCUMENTS

EP    0755655 A2    1/1997
EP    0755656 A2    1/1997
(Continued)

*Primary Examiner* — Vi X Nguyen
(74) *Attorney, Agent, or Firm* — Klarquist Sparkman, LLP (57) ABSTRACT

Described herein are reusable surgical needles having a resiliently collapsible rear loop that captures a suture as it is passed through an object and resiliently expands upon exiting the object to release the suture. Also described are suture spool assemblies that include a rigid housing and a rotatable spool of suture material suspended within the housing so that a plurality of sutures can be dispensed from the assembly in succession during a surgery. Also described are annular pledgets having diametrical dimensions similar to an outer ring of a cardiac implant such that a single annular pledget can be used with a plurality of sutures that secure the cardiac implant to native tissue around the perimeter of the cardiac implant. Related methods of suturing cardiac implants are also disclosed.

4 Claims, 9 Drawing Sheets

(52) U.S. Cl.
CPC ............ *A61B 2017/0464* (2013.01); *A61B 2017/06009* (2013.01); *A61F 2/2409* (2013.01)

(56) References Cited

U.S. PATENT DOCUMENTS

| | | |
|---|---|---|
| 7,083,628 B2 | 8/2006 | Bachman |
| 7,381,210 B2 | 6/2008 | Zarbatany et al. |
| 9,017,347 B2 | 4/2015 | Oba et al. |
| 9,498,202 B2 | 11/2016 | Jafari et al. |
| 2004/0204724 A1 | 10/2004 | Kissel et al. |
| 2005/0251209 A1 | 11/2005 | Saadat et al. |
| 2006/0089571 A1 | 4/2006 | Gertner |
| 2006/0265042 A1 | 11/2006 | Catanese et al. |
| 2006/0276871 A1 | 12/2006 | Lamson et al. |
| 2007/0005079 A1 | 1/2007 | Zarbatany et al. |
| 2007/0049970 A1 | 3/2007 | Belef et al. |
| 2007/0185497 A1* | 8/2007 | Cauthen ............ A61B 17/0057 606/99 |
| 2008/0154286 A1 | 6/2008 | Abbott et al. |
| 2012/0053599 A1 | 3/2012 | Shikhman et al. |
| 2012/0165865 A1 | 6/2012 | Fujisaki et al. |
| 2013/0165953 A1 | 6/2013 | Oba et al. |
| 2016/0183937 A1 | 6/2016 | Miraki et al. |

FOREIGN PATENT DOCUMENTS

| | | |
|---|---|---|
| EP | 1484023 A1 | 12/2004 |
| EP | 2455001 A2 | 5/2012 |
| EP | 2462876 A2 | 6/2012 |
| WO | 0128455 A1 | 4/2001 |

* cited by examiner

DEVICES AND METHODS FOR SUTURING A CARDIAC IMPLANT

FIELD

Described herein are devices and methods for suturing a cardiac implant using a surgical needle.

BACKGROUND

Needles are frequently used with a needle driver in many different surgical procedures, such as to close vascular tissues, during an aortotomy, and during heart valve surgery. These needles typically have a size and shape that is customized for each particular procedure. Such customized needles can be very expensive. During procedures, a surgeon often uses several different types of needles and sutures for different aspects of the procedure. The needles are typically used with one or more small reinforcing pledgets for each suture. The pledgets provide more resistance to the sutures and protect against the sutures cutting the tissue. However, during surgery, a suture occasionally breaks or pulls out of the needle, and as a consequence a pledget for that suture can come loose and can get lost inside the patient. During a cardiac valve replacement, for example, a surgeon may place 12-18 sutures within the native valve annulus, with each suture having a respective needle and its own respective pledget. The surgeon then drives each needle and respective suture through and anchorage part of the implant. Since each of the sutures is applied using a different needle, the cost of placing 12-18 sutures includes 12-18 times the cost of one needle.

SUMMARY

The disclosed devices and methods can reduce the total cost of the needles by using the same needle for all or many of the sutures, can eliminate or reduce the risk of losing pledgets within the patient's body, and/or can provide an alternative and easier way to place the needle/sutures within the tissue and cardiac implants.

An exemplary suture needle includes an elongated rigid body having a sharp front end for piercing and a flexible looped portion coupled to the rear end the rigid body. In some embodiments, the looped portion comprises four substantially linear segments linked together end-to-end with three bends joining the four linear segments such that the looped portion has a generally quadrilateral shape in an open configuration. The looped portion is resiliently collapsible from the open configuration to a collapsed configuration such that the surgical needle is adapted to capture a suture in the looped portion in the collapsed configuration while the surgical needle is drawn through a target object. The looped portion is then resiliently expandable from the collapsed configuration back to the open configuration, such that the surgical needle is adapted to release the captured suture from the looped portion after the surgical needle has drawn the suture through a target object.

An exemplary suture spool assembly comprises a rigid outer housing and at least one spool of suture material suspended within the outer housing such that the spool is free to rotate relative to the outer housing about a central axis of the spool. For each spool, the housing can include a suture outlet through which a free end of the suture material on the spool extends, such that tension on the free end of the suture material causes the spool to rotate and dispense the suture material from the spool through the suture outlet. The assembly can include two or more spools that each hold different kinds of suture material suture materials. The housing can be opened and closed to insert, remove and replace the spools.

Also described herein are annular pledgets having diametrical dimensions similar to an outer anchorage ring of a cardiac implant such that a single annular pledget can be used with the plurality of sutures that secure the cardiac implant to native tissue around the perimeter of the cardiac implant.

An exemplary method of securing a cardiac implant comprises dispensing a first suture from a suture spool assembly, inserting the first suture through an opening in a surgical needle, passing the surgical needle and first suture through a first native tissue implant location, passing the surgical needle and first suture through an annular pledget, passing the surgical needle and first suture through an outer anchorage portion of a cardiac implant, and securing the cardiac implant to the first native tissue implant location using the first suture, with the annular pledget positioned between the first native tissue implant location and the outer portion of a cardiac implant. The method can further include re-using the same needle to apply one or more additional sutures that secure the surgical implant to one or more respective additional native tissue locations, wherein the additional sutures pass through the same annular pledget. A single annular pledget can be used that has roughly the same diametrical dimensions as the outer anchorage portion of the cardiac implant.

The foregoing and other objects, features, and advantages of the disclosed technology will become more apparent from the following detailed description, which proceeds with reference to the accompanying figures.

DETAILED DESCRIPTION

Figure 1:
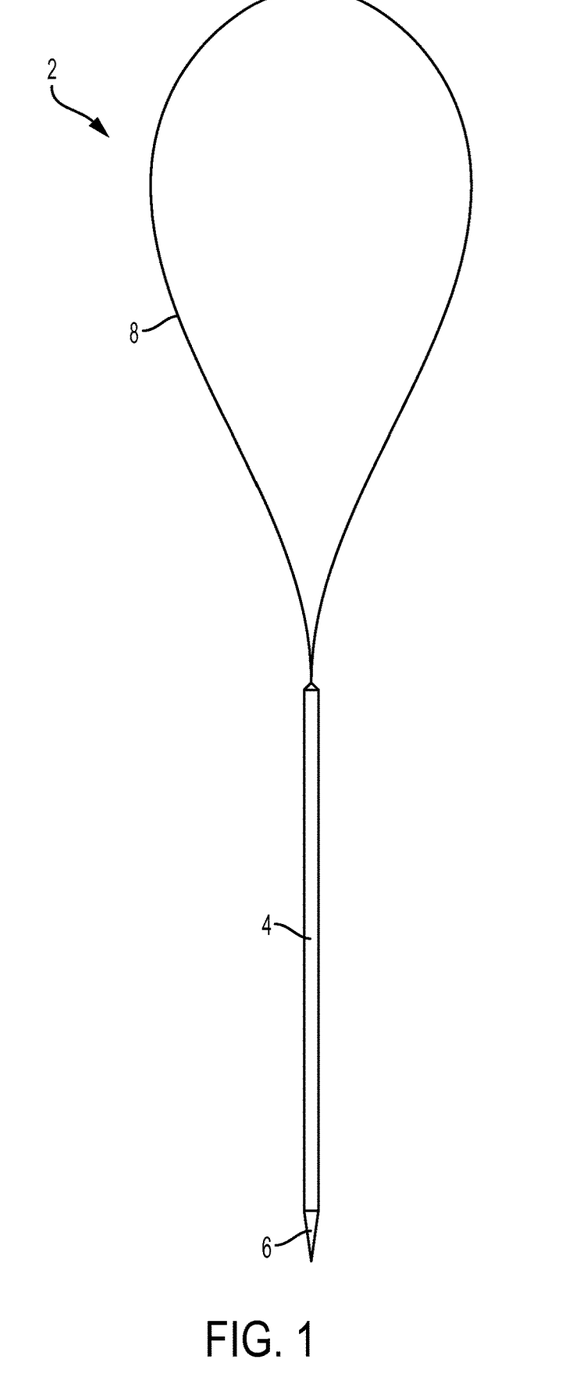
FIG. 1 shows an exemplary surgical needle with a straight body and a curved looped end.

FIG. 1 shows an exemplary needle 2 that comprises a body 4 with a sharp distal tip 6 at a distal or lead end and a loop 8 extending from the proximal or rear end. The body 4 can be solid or tubular, and can be made from any sufficiently strong material, such as stainless steel. In some embodiments, the body 4 is made from a sharpened solid wire, and in other embodiments the body 4 is made from a hypotube with a beveled tip. The body 4 can have a diameter and length selected to match the application for which it is intended. In one example, the body 4 can have an outer diameter of about 0.025 inch and a length of about 1.0 inch. The distal tip 6 can be beveled or otherwise sharpened to a point for puncturing tissue and an implant. The loop 8 can have a rounded, generally teardrop shape as shown in FIG. 1. The loop 8 can comprise a thin, flexible, resilient strand, such as a stainless steel wire, or can comprise other thin, strong, resilient material, such as polymeric material. The loop 8 can be attached to the body 4 in any secure manner, such as by welding (e.g., laser welding) or bonding the ends of the loop directly to the body, or by inserting ends of the loop into a hole or cavity in the proximal end of the body (e.g., with a tubular body or a solid body) and crimping the proximal end of the body onto the ends of the loop.

The loop 8 receives a suture (or sutures) such that the needle 2 can penetrate through tissue, a valve frame, sewing cuff, or other component of a prosthetic device, and carry the suture through the device. When the loop 8 passes through tissue or another object, the loop 8 collapses and grips the suture securely, preventing the suture from sliding out. The loop 8 can resiliently re-expand, at least partially, back to its original teardrop shape after passing through an object to release the suture and reload a new suture.

Figure 2:
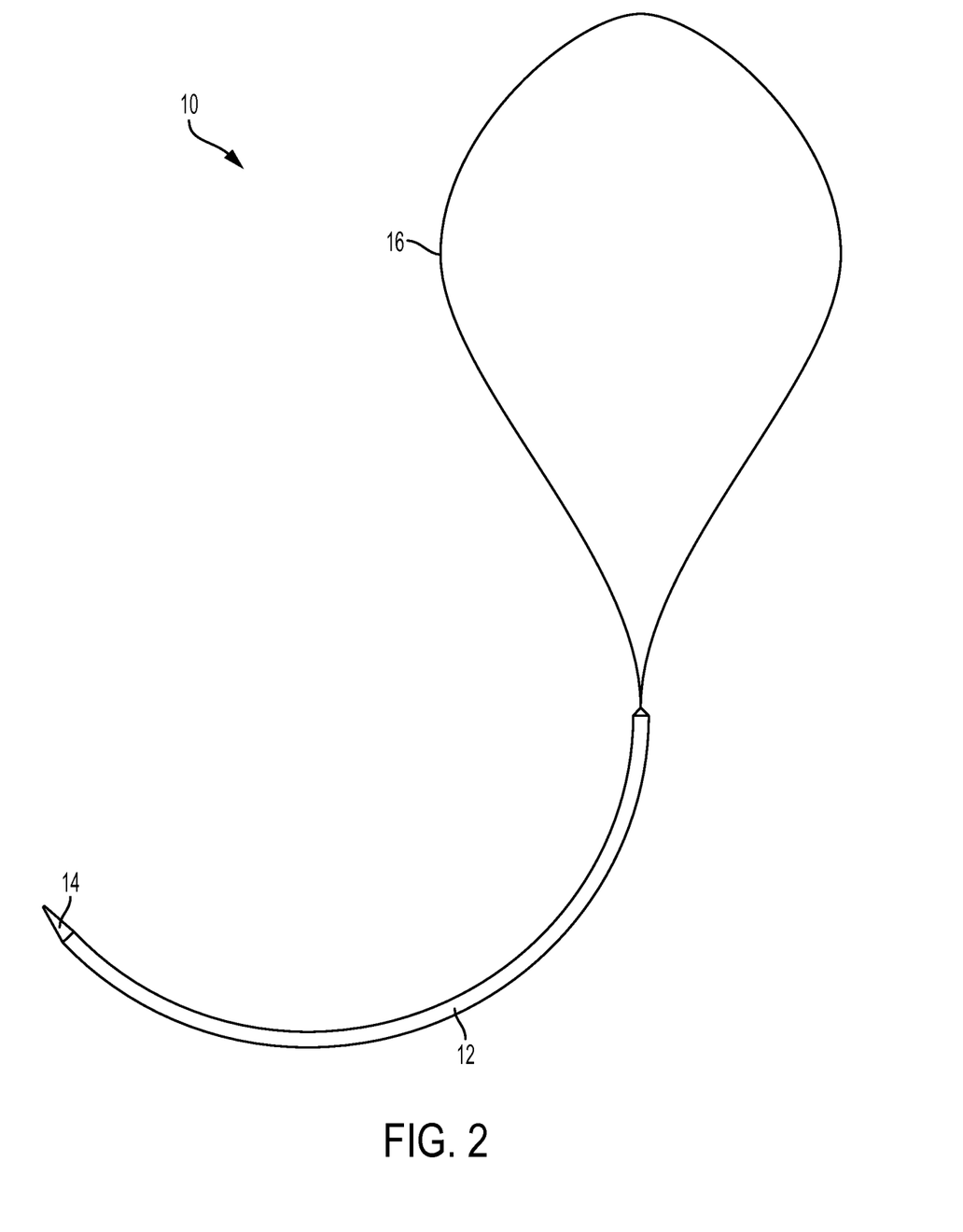
FIG. 2 shows an exemplary surgical needle with a curved body and a curved looped end.

FIG. 2 shows another exemplary needle 10 comprising a curved body 12 with a sharp distal tip 14 at the distal end and a loop 16 extending from the proximal end. The needle 10 is similar to the needle 2, except that the body 12 is curved. The curved body 12 can have any degree of curvature. For example, the body 12 can form a semi-circle, or a quarter of a circle, or other arcuate shapes.

Figure 3:
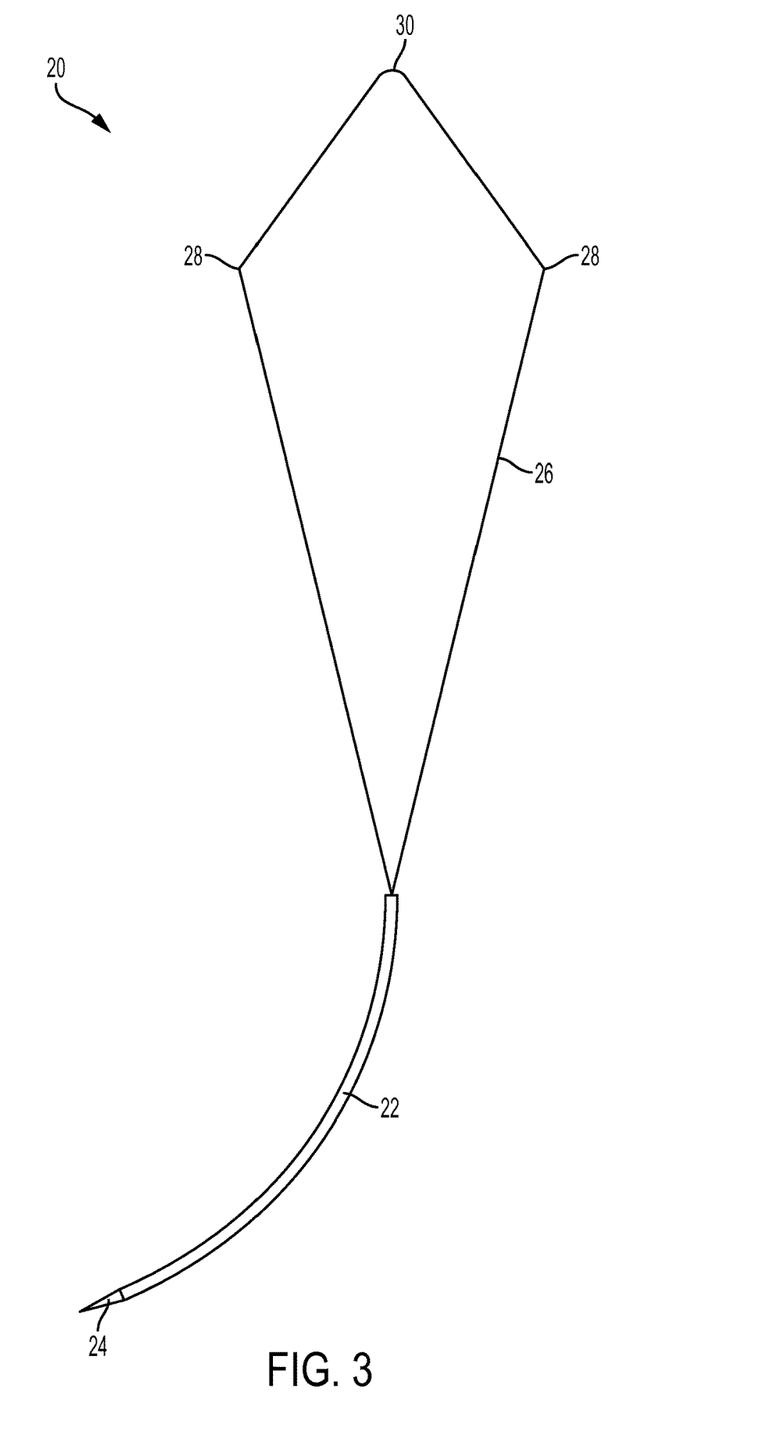
FIG. 3 shows an exemplary surgical needle with a curved body and a four-sided looped end.

FIG. 3 shows another exemplary needle 20 comprising a curved body 22 with a sharp distal tip 24 at the distal end and a loop 26 extending from the proximal end. The loop 26 includes substantially straight sides extending between angled bends 28 and 30, forming a generally diamond shape or kite shape. This shape can help the loop 26 re-open after passing through a narrow passage, such as after passing through a valve frame or sewing cuff. The two bends 28 can remain separated from each other even after the loop 26 has plastically deformed and collapsed to some degree following several passes through a valve frame or other object. Such resilient separation can allow a surgeon to continue to rethread sutures through the loop 26 over and over again until the surgery is complete, re-using the single needle for each suture. Many other loop shapes and configurations can also be used in other embodiments. In alternative embodiments, the rigid body 22 can be straight or can any other suitable curvature.

In general, a surgical needle can comprise an elongated rigid body having a sharp front end for piercing and a rear end, and a looped portion coupled to the rear end the rigid body. The looped portion can comprise four substantially linear segments linked together end-to-end with three bends joining the four linear segments such that the looped portion has a generally quadrilateral shape in an open configuration. The looped portion is resiliently collapsible from the open configuration to a collapsed configuration where the four linear segments are generally parallel and extending linearly from the rear end of the rigid body, such that the surgical needle is adapted to capture a suture between the four linear segments in the collapsed configuration while the surgical needle is drawn through a target object, such as a pledget and/or a cardiac implant. The looped portion is also resiliently expandable from the collapsed configuration back to the open configuration, such that the surgical needle is adapted to release the captured suture from between the four linear segments after the surgical needle has drawn the suture through a target object.

In some embodiments, the looped portion has a generally kite-shaped formation in the open configuration (like the shape shown in FIG. 3), wherein a first two of the four linear segments have substantially the same length, and a second two of the four linear segments have substantially the same length, but the first two linear segments have a different length than the second two linear segments. In some embodiments, the three bends in the looped portion each define an interior angle between the linear segments joined by the respective bend, and when the looped portion is in the collapsed configuration, a first of the three bends (e.g., bend 30 in FIG. 3) has an interior angle that is less than 10°, such as near 0°, and the other two of the three bends (e.g., bends 28 in FIG. 3) have an interior angle that is greater than 170°, such as near 180°.

Figure 4:
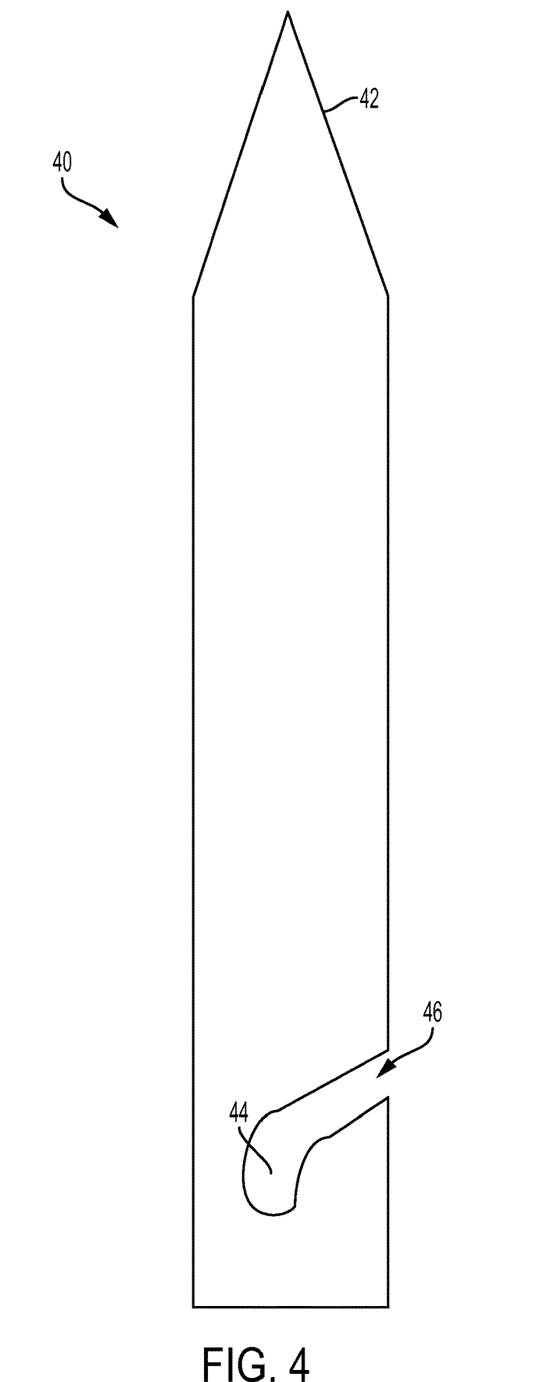
FIG. 4 shows an exemplary surgical needle with a straight body and slotted end.

FIG. 4 shows is a schematic side view of another exemplary needle 40 that comprises a sharp distal tip 42 and an angled slot 44 adjacent the proximal end for receiving a suture. The slot 44 can extend proximally from a lateral opening 46 such that a suture in the slot is restricted from exiting the slot while the needle 40 is passed through an object and the object applies proximally directed forces on the suture. In some such embodiments, the lateral opening 46 can be plastically closed after inserting a suture into the slot, and manually re-opened to release the suture and load another suture. The ability to load and remove a suture through laterally into and out of the slot 44 can obviate the need to thread an end of the suture through a loop, eyelet, or other enclosed opening to load and remove the suture. This can save time during the procedure and can allow the needle 40 to be applied onto or removed from a suture when neither end of the suture is free, such as with a looped portion of a suture or a suture with both ends extending into tissue or other objects.

Figure 5:
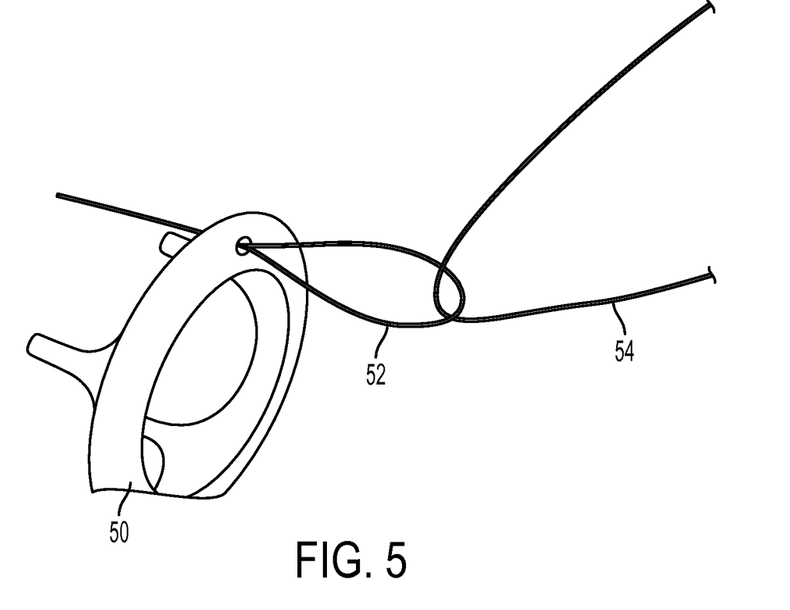
FIG. 5 shows an exemplary surgical needle passing a suture through an exemplary cardiac implant.
Figure 7:
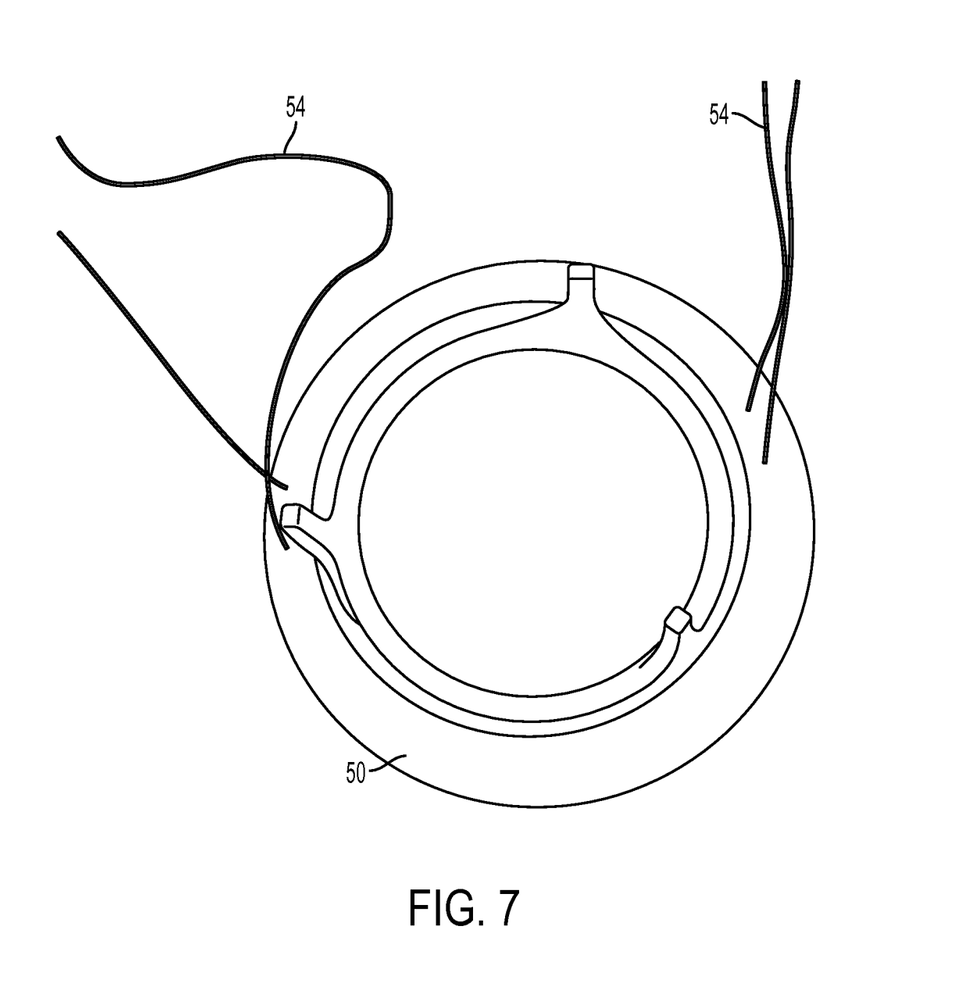
FIG. 7 is a top view of an exemplary cardiac implant with two pairs of sutures passing through its outer body.
Figure 8:
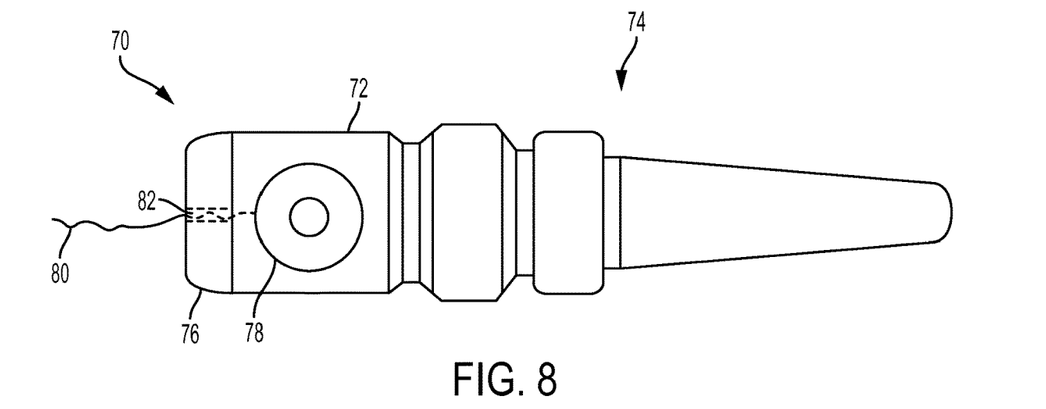
FIG. 8 is a schematic cross-sectional side view of an exemplary suture spool assembly, showing an internal suture spool and a suture passing from the spool through an aperture out of the assembly.

FIG. 5 shows an exemplary needle 52 (similar to the needle 2 in FIG. 1) passing through an outer annular portion of a cardiac implant 50 (e.g., a sewing ring of a prosthetic heart valve) while loaded with a suture 54. The suture 54 passes through a proximal loop portion of the needle 52 while a sharpened distal end has already puncture the implant 50. FIG. 7 shows the exemplary cardiac implant 50 from a top view after several sutures 54 have been threaded through it. Any of the needles disclosed herein can be loaded with a variety of different types of sutures. For example, the sutures can vary in material, size, and/or color.

Figure 6:
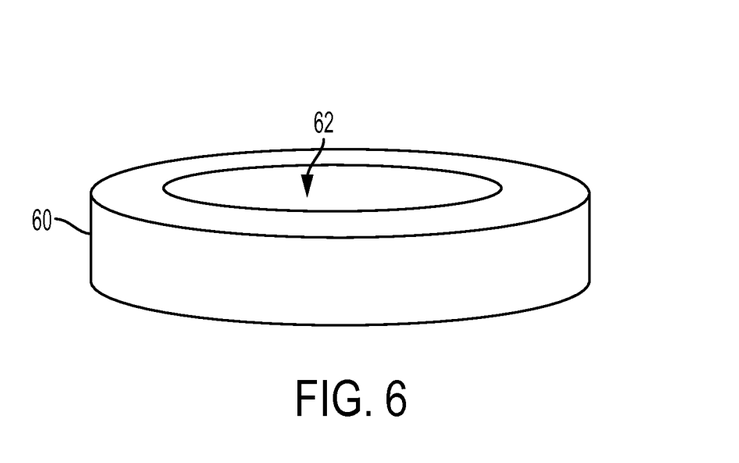
FIG. 6 shows an exemplary annular pledget.

FIG. 6 shows an exemplary pledget 60 that can be used in place of a plurality of smaller individual pledgets. The pledget 60 comprises an annular body with a central opening 62. The annular body of the pledget 60 can be sized to correspond with the diameter of a particular cardiac implant, such as the cardiac implant 50 in FIG. 5, with the central opening 62 being aligned with the flow pathway through the cardiac implant. The pledget 60 can be placed along the lower surface of the implant such that a plurality of sutures (e.g., all 12-18 sutures) can pass through the single pledget 60 and then through the cardiac implant. If one of the sutures breaks or comes loose, the pledget 60 is still retained by the other sutures and it is less prone to become lost inside of the patient like individual smaller pledgets for each suture. The pledget 60 can be made of any suitable material (e.g., Teflon®) and can have any shape and size to correspond with the suture pattern for a particular implant. For example, the pledget may have a D-shape for a mitral valve implant.

Figure 9:
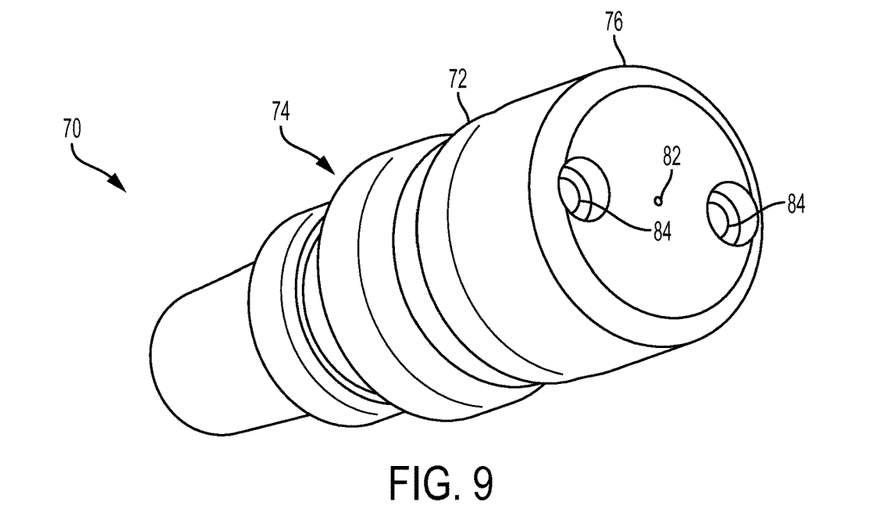
FIG. 9 is a perspective view of the suture spool assembly of FIG. 8.
Figure 10:
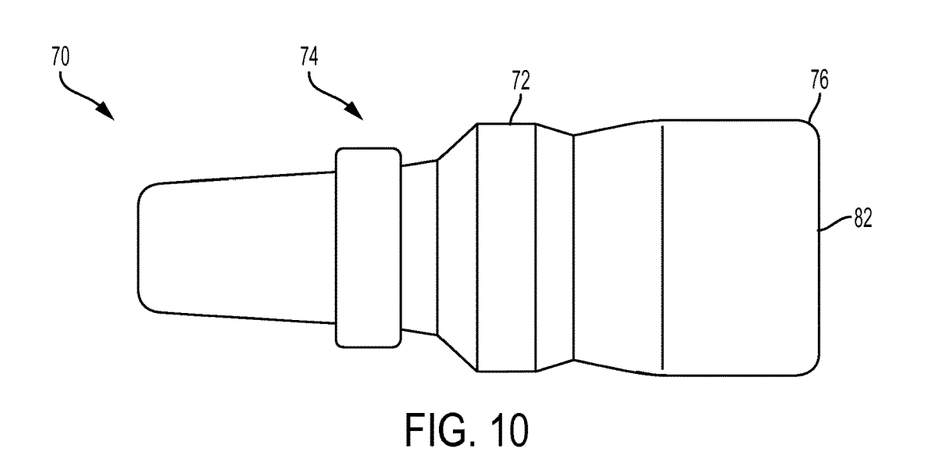
FIG. 10 is a side view of the suture spool assembly of FIG. 8.
Figure 11:
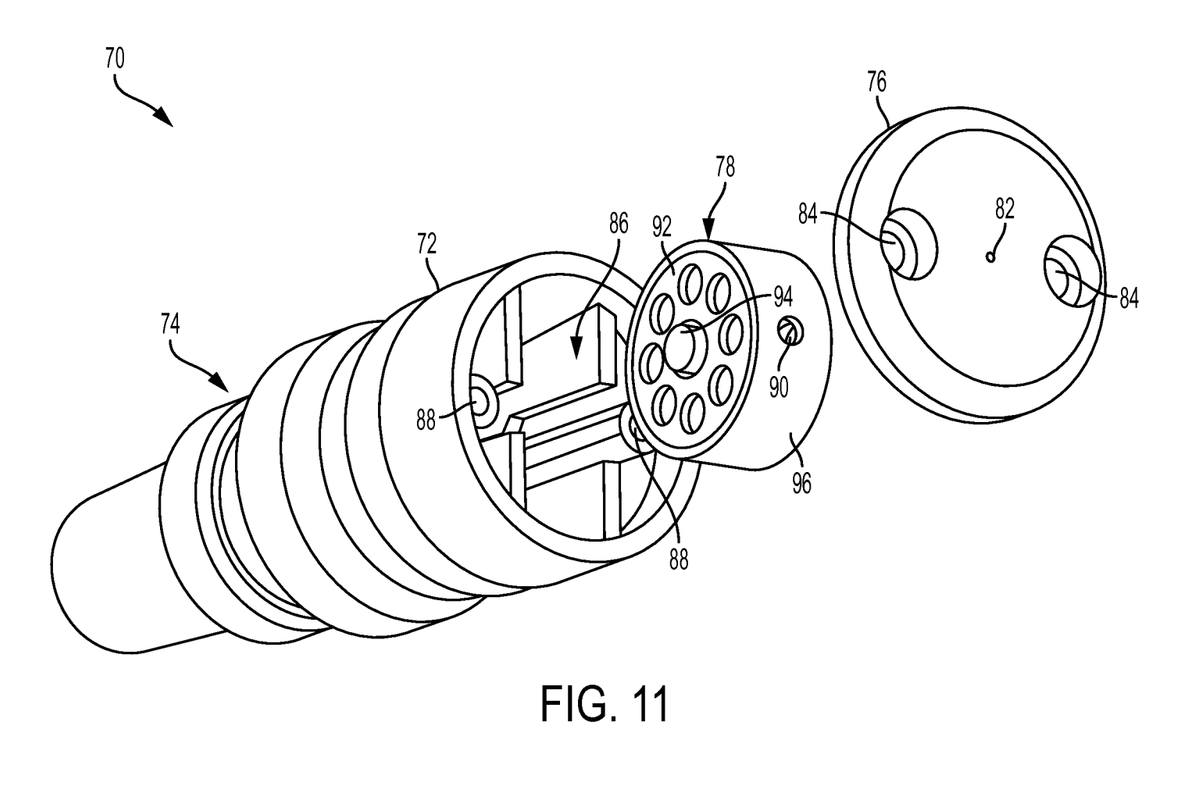
FIG. 11 is an exploded perspective view of the suture spool assembly of FIG. 8.

FIGS. 8-12 illustrate an exemplary suture spool assembly 70 that can be used to contain and dispense sutures for quick and easy access during implantation of cardiac implants. The assembly 70 can comprise a housing 72 that forms a handle portion 74 at one end and houses one or more spools 78 of sutures. A cap 76 can close off the opposite end and include an opening 82 to allow the suture 80 to extend out of the assembly to be dispensed. The cap 76 can include a blade or other cutting element to cut the suture when a desired length has been pulled out. As shown in FIGS. 9 and 11, the cap 76 can be secured to the housing 72 via fasteners (e.g., screws) passing through openings 84 and 88.

Figure 12:
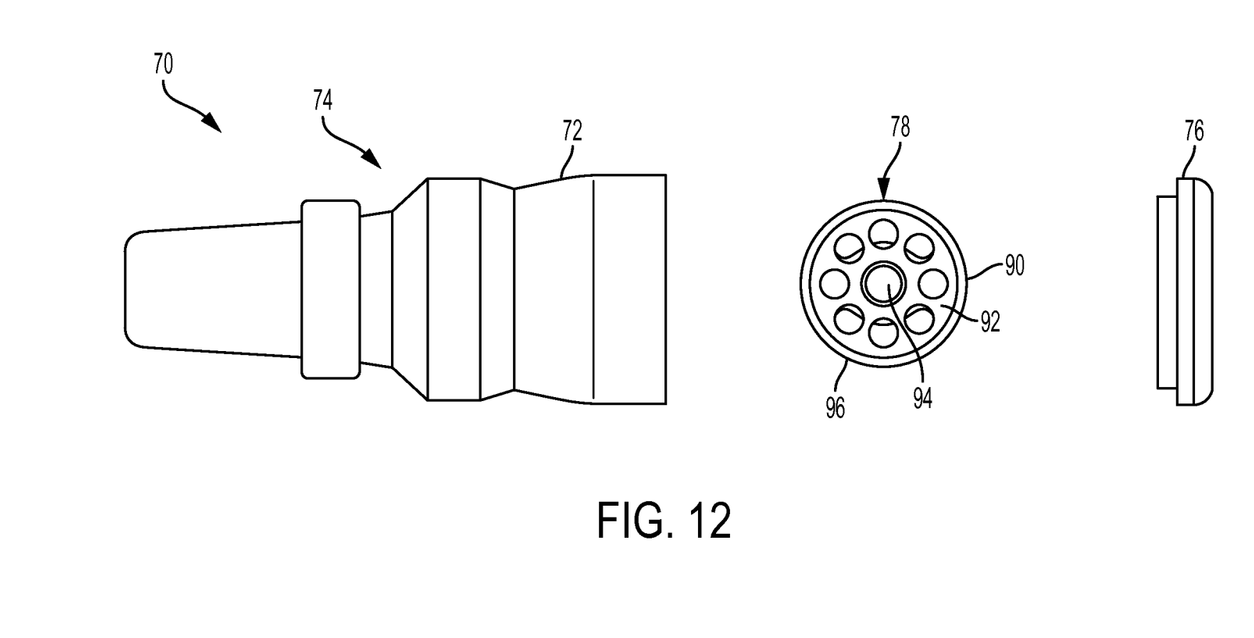
FIG. 12 is an exploded side view of the suture spool assembly of FIG. 8.

As shown in FIGS. 11 and 12, at least one spool 78 can be mounted within a cavity 86 inside the housing 72. Each spool 78 can include an outer body 96 that does not rotate relative to the housing 72 and an inner body 92 that rotates within the outer body about an axle 94. The inner body 92 can be loaded with the suture material and the leading end of the suture material can pass through an opening 90 in the outer body 96 and out through the opening 82 in the cap 76 to be dispensed. In embodiments having more than one spool, the spools can be oriented side-by-side and the cap 76 can include a corresponding number of opening 82 to dispense each different suture from. Each different suture and/or the spools themselves can have a different color for visual identification. In some embodiments, the plural spools can share a common rotation axle, with in other embodiment, individual axles are included. Each spool can be winded with any length of suture material, such as about 10-30 feet, or about 20-25 feet, of suture material. The total length on the spool can be sufficient to supply material for all the sutures needed to complete a given procedure. The cap 76 can be easily removed and replaced to load, remove, or swap out the spools.

During surgery, the user can dispense a length of suture material from the suture spool assembly 70 for a first suture, cut the suture material to the desired length, insert the suture material into the needle, pass the needle and suture through the tissue where the cardiac implant is to be secured, pass the needle and suture through the pledget and the cardiac implant, release the suture from the needle, secure the suture to secure the implant to the tissue, then repeat the process for each suture location using the same needle for each suture.

The disclosed devices, systems, and methods can be used with various types of sutures, threads, cords, wires, cables, lines, filaments, or similar objects (which are collectively referred to herein as "sutures" for ease of description). Exemplary suture materials can include biological tissues (e.g., collagen-based tissue), polyglycolide, polydioxanone, polyester, nylon, polypropylene, and other polymeric materials. Some sutures comprise several strands of fibers braided or woven together. Any suitable materials can be used in the construction of the needles, pledgets, suture spools, suture dispensers, and/or other devices disclosed herein.

For purposes of this description, certain aspects, advantages, and novel features of the embodiments of this disclosure are described herein. The disclosed methods, devices, and systems should not be construed as limiting in any way. Instead, the present disclosure is directed toward all novel and nonobvious features and aspects of the various disclosed embodiments, alone and in various combinations and subcombinations with one another. The methods, devices, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the term "and/or" used in a list of elements means any one or more of the listed elements. For example, the phrase "A, B, and/or C" means "A," "B," "C," "A and B," "A and C," "B and C" or "A, B and C."

As used herein, the term "coupled" generally means physically linked and does not exclude the presence of intermediate elements between the coupled items absent specific contrary language.

In view of the many possible embodiments to which the principles disclosed herein may be applied, it should be recognized that the illustrated embodiments are only preferred examples and should not be taken as limiting the scope of the disclosure. The scope of this disclose is at least as broad as the scope of the following claims. I therefore claim all that comes with the scope of these claims.

The invention claimed is:

1. A method of securing a cardiac implant, comprising:
dispensing a first suture from a suture spool assembly;
inserting the first suture through a resiliently collapsible and expandable looped portion of a surgical needle;
passing the surgical needle and first suture through a first native tissue implant location;
passing the surgical needle and first suture through an annular pledget;
passing the surgical needle and first suture through an outer portion of a cardiac implant;
securing the cardiac implant to the first native tissue implant location using the first suture, with the annular pledget positioned between the first native tissue implant location and the outer portion of a cardiac implant;
dispensing a second suture from the suture spool assembly;
inserting the second suture through the looped portion of the surgical needle;
passing the surgical needle and second suture through a second native tissue implant location;
passing the surgical needle and second suture through the annular pledget;
passing the surgical needle and second suture through the outer portion of the cardiac implant; and
securing the cardiac implant to the second native tissue implant location using the second suture, with the annular pledget positioned between the second native tissue implant location and the outer portion of a cardiac implant.

2. The method of claim 1, wherein the outer portion of the cardiac implant comprises an annular ring and the annular pledget is commensurate in diameter with the annular ring of the cardiac implant.

3. The method of claim 1, wherein dispensing the first suture comprises pulling a length of suture from a spool of suture material out of the suture spool assembly and cutting the length of suture from the remainder of the suture material on the spool.

4. The method of claim 1, wherein passing the surgical needle and the first suture through the outer portion of the cardiac implant comprises:
   causing the looped portion of the surgical needle to resiliently collapse around the first suture as the surgical needle pulls the first suture through the outer portion of the cardiac implant; and
   allowing the looped portion of the surgical needle to resiliently expand to release the first suture after the surgical needle and the first suture have passed through the outer portion of the surgical implant.

* * * * *